(12) United States Patent
Sun et al.

(10) Patent No.: US 12,174,156 B1
(45) Date of Patent: Dec. 24, 2024

(54) DEVICE FOR TESTING REACTION BETWEEN SUPERCRITICAL CARBON DIOXIDE AND ROCK

(71) Applicant: Northeast Petroleum University, Daqing (CN)

(72) Inventors: Mengdi Sun, Daqing (CN); Zhejun Pan, Daqing (CN); Tong Wu, Daqing (CN); Bo Liu, Daqing (CN); Minghan Li, Daqing (CN)

(73) Assignee: Northeast Petroleum University, Daqing (CN)

(*) Notice: Subject to any disclaimer, the term of this patent is extended or adjusted under 35 U.S.C. 154(b) by 0 days.

(21) Appl. No.: 18/774,968

(22) Filed: Jul. 17, 2024

(30) Foreign Application Priority Data

Aug. 16, 2023 (CN) .......................... 202311030410.6

(51) Int. Cl.
   *G01N 33/24* (2006.01)
   *G01B 11/26* (2006.01)
   *G01N 3/56* (2006.01)

(52) U.S. Cl.
   CPC ............. *G01N 3/567* (2013.01); *G01B 11/26* (2013.01); *G01N 33/24* (2013.01); *G01N 2203/0226* (2013.01); *G01N 2203/0232* (2013.01); *G01N 2203/0647* (2013.01)

(58) Field of Classification Search
   CPC ................... G01N 3/567; G01N 33/24; G01N 2203/0226; G01N 2203/0232; G01N 2203/0647; G01B 11/26
   USPC ......... 73/7, 53.01, 64.49, 64.52, 64.56, 866; 348/61, 79, 80, 82, 135
   See application file for complete search history.

(56) References Cited

U.S. PATENT DOCUMENTS

2022/0390342 A1* 12/2022 Li ............................ G01N 1/38

FOREIGN PATENT DOCUMENTS

CN           112326484 A       2/2021

OTHER PUBLICATIONS

First Office Action received in CN Application No. 202311030410.6, Dated Feb. 5, 2024, pp. 13.
Ye Ziqiang, "Design of static and dynamic contact angle measuring device under high temperature and high pressure environment", Masteral Dissertation, Dalian University of Technology, 47 pages.

* cited by examiner

*Primary Examiner* — Robert R Raevis
(74) *Attorney, Agent, or Firm* — Gearhart Law, LLC (57) ABSTRACT

Provided is a device for testing a reaction between supercritical carbon dioxide and a rock. The device includes a carbon dioxide pressurization system, a reaction system, a contact angle test system and an observation system. The carbon dioxide pressurization system is configured to liquefy, heat and vaporize an initial carbon dioxide gas to obtain gaseous carbon dioxide. The reaction system is configured to regulate and control a temperature and pressure to change a state of the gaseous state to obtain supercritical carbon dioxide, and to enable the supercritical carbon dioxide to react with a sample. The contact angle test system is configured to convey a reaction residual water source and receive residual supercritical carbon dioxide, and to carry out a contact reaction of the residual supercritical carbon dioxide, the sample and the reaction residual water source.

7 Claims, 3 Drawing Sheets

DEVICE FOR TESTING REACTION BETWEEN SUPERCRITICAL CARBON DIOXIDE AND ROCK

CROSS-REFERENCE TO RELATED APPLICATION

This patent application claims the benefit and priority of Chinese Patent Application No. 202311030410.6, entitled "DEVICE FOR TESTING REACTION BETWEEN SUPERCRITICAL CARBON DIOXIDE AND ROCK" filed on Aug. 16, 2023, the disclosure of which is incorporated by reference herein in its entirety as part of the present application.

TECHNICAL FIELD

The present disclosure relates to the technical field of unconventional petroleum experimental testing, and in particular to a device for testing a reaction between supercritical carbon dioxide and a rock.

BACKGROUND

Global warming has always been regarded as a key problem facing mankind. The emission of greenhouse gas carbon dioxide is the main cause of climate change and environmental problems. In order to control the increasing emission and concentration of carbon dioxide in the atmosphere, mitigation of climate change can be achieved through carbon capture, utilization and storage (CCUS). Deep unmineable coal seams, and coal seams and shale beds capable of providing gas recovery are important reservoirs for carbon dioxide storage, which are also of great significance for achieving "carbon peaking and carbon neutrality". The coal seams and the shale beds can capture carbon dioxide through solubility capture and mineral capture. It is of great significance to study the storage and transport mechanism of the carbon dioxide in shale or coal reservoirs for carbon dioxide storage, and production of shale gas and coalbed methane. Meanwhile, it is of great significance to study the liquid spreading in the carbon dioxide atmosphere for improving the shale gas and coalbed methane. Shale reservoirs and the coal seams are in the extreme environment of high temperature and high pressure, so it is necessary to characterize the storage and transportation conditions of carbon dioxide in the shale and coal under high-temperature and high-pressure environment and the influence of supercritical carbon dioxide on a liquid contact angle under different temperature and pressure conditions through experiments.

At present, carbon dioxide storage is mainly studied by means of simulation. However, the simulation method lacks the support of real experimental data and has limited reliability, so it is necessary to study the storage and transportation of supercritical carbon dioxide by experimental methods. Meanwhile, the competition and adsorption conditions of liquid in the shale or coal by supercritical carbon dioxide injection are studied. Under the experimental conditions of the traditional contact angle device, the degree of wetting can only be measured by making a gas-liquid interface tangent at the intersection of solid, liquid and gas at normal temperature and pressure, and the requirement of measuring the degree of wetting of the sample in situ in the supercritical carbon dioxide environment under different temperature and pressure conditions cannot be achieved.

SUMMARY

The embodiments aim to provide a device for testing a reaction between supercritical carbon dioxide and a rock, which can achieve the requirement of an in-situ measurement of the degree of wetting in a supercritical carbon dioxide environment under different temperature and pressure conditions.

In order to achieve the objective above-mentioned, the present disclosure provides the following solutions.

A device for testing a reaction between supercritical carbon dioxide and a rock includes:
  a carbon dioxide pressurization system configured to liquefy, heat and vaporize an initial carbon dioxide gas to obtain gaseous carbon dioxide;
  a reaction system connected with the carbon dioxide pressurization system and configured to regulate and control a temperature and a pressure to change a state of the gaseous carbon dioxide to obtain the supercritical carbon dioxide, and to enable the supercritical carbon dioxide to react with a sample, so as to obtain reaction products, where the reaction products include a reaction residual water source, a reaction sample and residual supercritical carbon dioxide;
  a contact angle test system connected with the reaction system and configured to convey the reaction residual water source, to receive the residual supercritical carbon dioxide, and to carry out a contact reaction of the residual supercritical carbon dioxide, the sample and the reaction residual water source; and
  an observation system connected with the contact angle test system and configured to acquire an included angle between the reaction residual water source and the sample when the contact reaction is carried out in the contact angle test system, where the included angle is configured to characterize a measure of a degree of wetting of an in-situ measurement in a supercritical carbon dioxide environment.

Alternatively, the carbon dioxide pressurization system includes:
  a low-temperature constant-temperature water bath box configured to liquefy the initial carbon dioxide gas to obtain liquefied carbon dioxide; and
  a preheater connected with the low-temperature constant-temperature water bath box and configured to heat and vaporize the liquefied carbon dioxide to obtain the gaseous carbon dioxide.

Alternatively, the carbon dioxide pressurization system further includes:
  a carbon dioxide gas cylinder configured to provide the initial carbon dioxide gas; and
  a filter connected with the carbon dioxide gas cylinder, and configured to filter the initial carbon dioxide gas, and to convey the filtered carbon dioxide gas to the low-temperature constant-temperature water bath box.

Alternatively, the reaction system further includes a high-temperature high-pressure magnetic stirrer reactor, a thermometer, a temperature controller, a pressure regulating valve and a pressure sensor.

The high-temperature high-pressure magnetic stirrer reactor is connected with the carbon dioxide pressurization system. The thermometer is arranged inside the high-temperature high-pressure magnetic stirrer reactor. The temperature controller is arranged outside the high-temperature high-pressure magnetic stirrer reactor and is connected with the high-temperature high-pressure magnetic stirrer reactor. The pressure regulating valve is connected with the high-temperature high-pressure magnetic stirrer reactor, and the pressure sensor is connected with the pressure regulating valve.

The thermometer is configured to measure a temperature in the high-temperature high-pressure magnetic stirrer reactor.

The temperature controller is configured to regulate and control the temperature in the high-temperature high-pressure magnetic stirrer reactor.

The pressure regulating valve is configured to regulate and control a pressure in the high-temperature high-pressure magnetic stirrer reactor.

The pressure sensor is configured to measure the pressure in the high-temperature high-pressure magnetic stirrer reactor.

The high-temperature high-pressure magnetic stirrer reactor is configured to receive the gaseous carbon dioxide, and the sample is placed in the high-temperature high-pressure magnetic stirrer reactor. The state of the gaseous carbon dioxide in the high-temperature high-pressure magnetic stirrer reactor is changed to obtain the supercritical carbon dioxide. In the high-temperature high-pressure magnetic stirrer reactor, the supercritical carbon dioxide reacts with the sample to obtain the reaction products.

Alternatively, the contact angle test system includes:
a drip valve connected with the reaction system and configured to convey the reaction residual water source; and
a contact-angle high-pressure chamber connected with the reaction system and the drip valve and configured to receive the residual supercritical carbon dioxide and the reaction residual water source, and to carry out a contact reaction of the residual supercritical carbon dioxide, the sample and the reaction residual water source.

Alternatively, the contact angle test system further includes:
a water tank configured to store tap water;
an advection pump connected with the water tank and configured to load the tap water according to a set flow rate; and
a piston container connected with the advection pump, the drip valve and the high-temperature high-pressure magnetic stirrer reactor, and configured to receive the reaction residual water source and to convey the reaction residual water source to the drip valve by means of a pressure of loading the tap water by the advection pump.

Alternatively, the observation system includes:
a camera connected with the contact angle test system and configured to acquire a sample surface image when the contact reaction is carried out in the contact angle test system;
and
a processing module connected with the camera and configured to determine the included angle between a water source and the sample according to the sample surface image.

Alternatively, the observation system further includes a light source.

The light source is arranged outside the contact angle test system and is configured to provide light for the camera.

According to specific embodiments, the embodiments have the following technical effects.

The device for testing a reaction between supercritical carbon dioxide and a rock is provided. A carbon dioxide pressurization system is configured to liquefy, heat and vaporize an initial carbon dioxide gas to obtain gaseous carbon dioxide. A reaction system is configured to regulate and control a temperature and pressure to change a state of the gaseous state to obtain supercritical carbon dioxide, and to enable the supercritical carbon dioxide to react with a sample. A contact angle test system is configured to convey a reaction residual water source and receive residual supercritical carbon dioxide, and to carry out a contact reaction of the residual supercritical carbon dioxide, the sample and the reaction residual water source. An observation system is configured to acquire an included angle between the reaction residual water source and the sample when the contact reaction is carried out in the contact angle test system. The requirement of the in-situ measurement of the degree of wetting in a supercritical carbon dioxide environment can be achieved under different temperature and pressure conditions.

BRIEF DESCRIPTION OF THE DRAWINGS

To describe the technical solutions in the embodiments of the present disclosure or in the prior art more clearly, the following briefly introduces the accompanying drawings required for describing the embodiments. Apparently, the accompanying drawings in the following description show merely some embodiments of the present disclosure, and those of ordinary skill in the art may still derive other drawings from these accompanying drawings without creative efforts.

LIST OF THE REFERENCE CHARACTERS 1 carbon dioxide pressurization system; 2 reaction system; 3 contact angle test system; 4 observation system; 5 carbon dioxide gas cylinder; 6 filter; 7 first switch; 8 low-temperature constant-temperature water bath box; 9 carbon dioxide storage tank; 10 pressure gauge; 11 first emptying valve; 12 plunger pump; 13 second switch; 14 second emptying valve; 15 check valve; 16 electric contact pressure gauge; 17 preheater; 18 third switch; 19 temperature control instrument; 20 third emptying valve; 21 fourth switch; 22 safety valve; 23 first pressure sensor; 24 resistor; 25 high-temperature high-pressure magnetic stirrer reactor; 26 thermometer; 27 temperature controller; 28 precooler; 29 backpressure valve; 30 outlet; 31 fourth emptying valve; 32 fifth switch; 33 sixth switch; 34 pressure regulating valve; 35 pressure sensor; 36 drip valve; 37 contact angle high-pressure chamber; 38 light source; 39 seventh switch; 40 eighth switch; 41 piston container; 42 ninth switch; 43 fifth emptying valve; 44 advection pump, 45 water tank; 46 camera.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts shall fall within the protection scope of the present disclosure.

In order to solve the problem in the prior art, a device for testing a reaction between supercritical carbon dioxide and a rock and testing a contact angle of fluids after reaction in situ is designed. By changing the temperature and the pressure, the device can measure competition and adsorption conditions of injected liquid on a sample in a supercritical carbon dioxide environment in situ. Meanwhile, a reaction experiment of the supercritical carbon dioxide and the rock can also be carried out to study the changes of the supercritical carbon dioxide and the rock after the reaction, thus finding an effective way to store carbon dioxide in the rock.

The embodiments aim to provide a device for testing a reaction between supercritical carbon dioxide and a rock, which can achieve the requirement of an in-situ measurement of a degree of wetting in a supercritical carbon dioxide environment under different temperature and pressure conditions.

To make the objectives, features and advantages of the present disclosure more apparently and understandably, the following further describes the present disclosure in detail with reference to the accompanying drawings and the specific embodiments.

Figure 1:
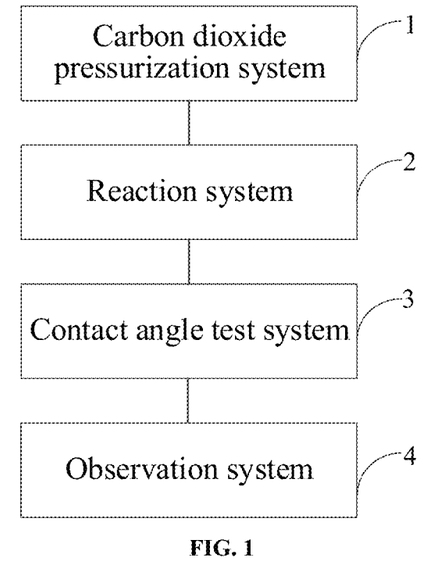
FIG. 1 is a structural block diagram of a device for testing a reaction between supercritical carbon dioxide and a rock according to an embodiment of the present disclosure.
Figure 2:
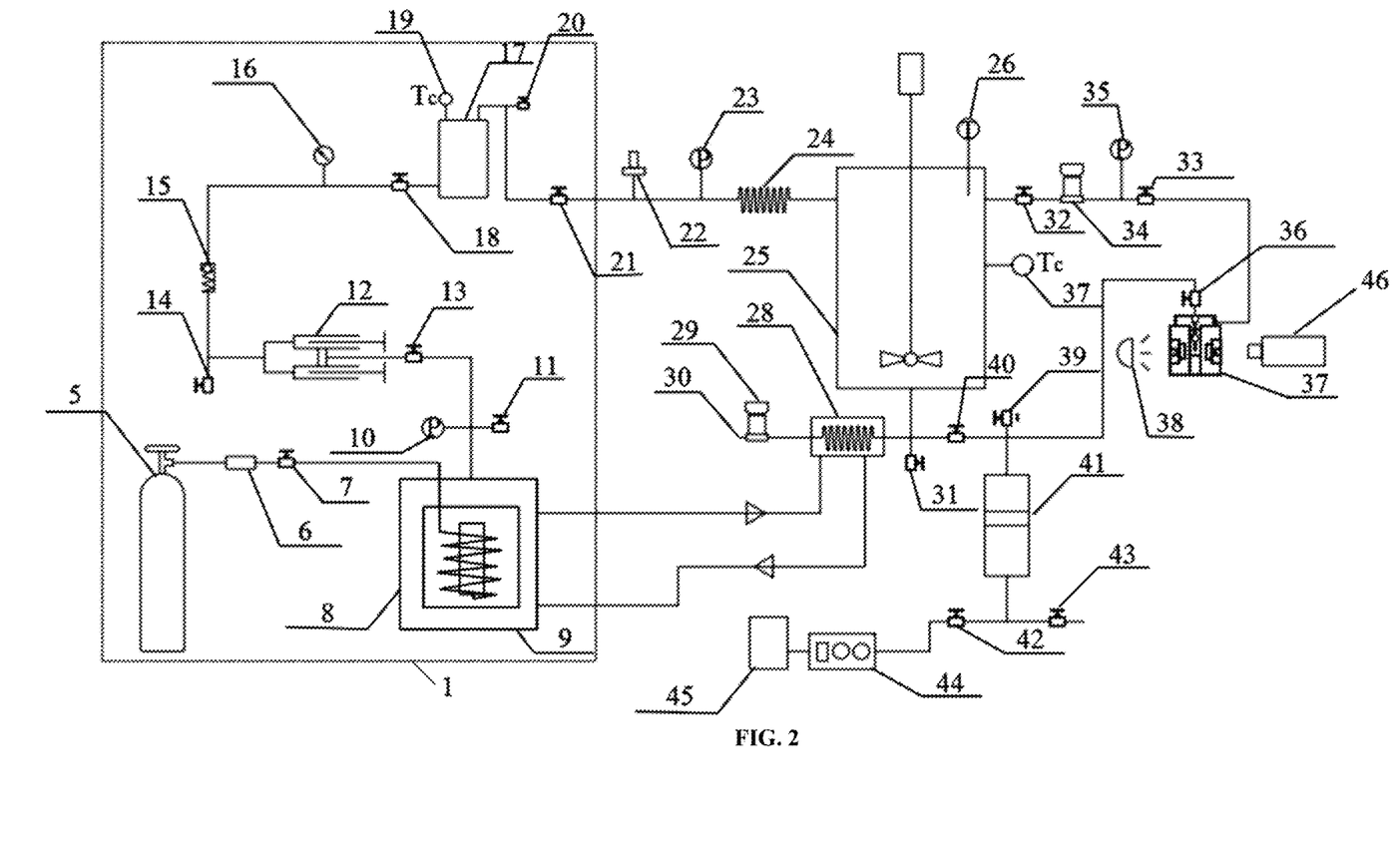
FIG. 2 is a structural diagram of the device for testing a reaction between supercritical carbon dioxide and a rock according to the embodiment of the present disclosure.

As shown in FIG. 1 and FIG. 2, a device for testing a reaction between supercritical carbon dioxide and a rock is provided by an embodiment of the present disclosure. The device includes a carbon dioxide pressurization system 1, a reaction system 2, a contact angle test system 3 and an observation system 4.

The carbon dioxide pressurization system 1 is configured to liquefy, heat and vaporize an initial carbon dioxide gas to obtain gaseous carbon dioxide.

The carbon dioxide pressurization system 1 includes a low-temperature constant-temperature water bath box 8 and a preheater 17.

The low-temperature constant-temperature water bath box 8 is configured to liquefy the initial carbon dioxide gas to obtain liquefied carbon dioxide.

The preheater 17 is connected with the low-temperature constant-temperature water bath box and is configured to heat and vaporize the liquefied carbon dioxide to obtain the gaseous carbon dioxide.

In an embodiment, the carbon dioxide pressurization system 1 further includes a carbon dioxide gas cylinder 5 and a filter 6.

The carbon dioxide gas cylinder 5 is configured to provide the initial carbon dioxide gas.

The filter 6 is connected with the carbon dioxide gas cylinder 5 and is configured to filter the initial carbon dioxide gas and convey the filtered initial carbon dioxide gas to the low-temperature constant-temperature water bath box 8.

The reaction system 2 is connected with the carbon dioxide pressurization system 1 and is configured to regulate and control a temperature and a pressure to change a state of the gaseous carbon dioxide to obtain supercritical carbon dioxide, and to enable the supercritical carbon dioxide to react with a sample, so as to obtain reaction products. The reaction products include a reaction residual water source, a reaction sample and residual supercritical carbon dioxide.

The reaction system 2 includes a high-temperature high-pressure magnetic stirrer reactor 25, a thermometer 26, a temperature controller 27, a pressure regulating valve 34 and a pressure sensor 35.

The high-temperature high-pressure magnetic stirrer reactor 25 is connected with the carbon dioxide pressurization system 1. The thermometer 26 is arranged inside the high-temperature high-pressure magnetic stirrer reactor 25. The temperature controller 27 is arranged outside the high-temperature high-pressure magnetic stirrer reactor 25 and is connected with the high-temperature high-pressure magnetic stirrer reactor 25. The pressure regulating valve 34 is connected with the high-temperature high-pressure magnetic stirrer reactor 25. The pressure sensor 35 is connected with the pressure regulating valve 34.

The thermometer 26 is configured to measure a temperature in the high-temperature high-pressure magnetic stirrer reactor 25.

The temperature controller 27 is configured to regulate and control the temperature in the high-temperature high-pressure magnetic stirrer reactor 25.

The pressure regulating valve 34 is configured to regulate and control a pressure in the high-temperature high-pressure magnetic stirrer reactor 25. The pressure sensor 35 is configured to measure the pressure in the high-temperature high-pressure magnetic stirrer reactor 25.

The high-temperature high-pressure magnetic stirrer reactor 25 is configured to receive the gaseous carbon dioxide, and a sample is placed in the high-temperature high-pressure magnetic stirrer reactor 25. The state of the gaseous carbon dioxide in the high-temperature high-pressure magnetic stirrer reactor 25 is changed to obtain the supercritical carbon dioxide. In the high-temperature high-pressure magnetic stirrer reactor 25, the supercritical carbon dioxide reacts with the sample to obtain the reaction products.

The contact angle test system 3 is connected with the reaction system 2 and is configured to convey the reaction residual water source and receive the residual supercritical carbon dioxide, and to carry out a contact reaction of the residual supercritical carbon dioxide, the sample and the reaction residual water source.

The contact angle test system 3 includes a drip valve 36 and a contact angle high-pressure chamber 37.

The drip valve 36 is configured to convey the reaction residual water source. The contact angle reaction chamber 37 is connected with the reaction system 2 and the drip valve 36 and is configured to receive the residual supercritical carbon dioxide and the reaction residual water source, and to carry out the contact reaction of the residual supercritical carbon dioxide, the sample and the reaction residual water source.

In an embodiment, the contact angle test system 3 further includes a water tank 45, an advection pump 44 and a piston container 41.

The water tank 45 is configured to store tap water and is capable of pressurizing the piston container 41. The advection pump 44 is connected with the water tank 45 and is configured to load the tap water according to a set flow rate. The piston container 41 is connected with the advection pump 44, the drip valve 36 and the high-temperature high-pressure magnetic stirrer reactor 25. The piston container 41 is configured to receive the reaction residual water source in the high-temperature high-pressure magnetic stirrer reactor 25 and to convey the reaction residual water source to the drip valve 36.

That is, residual liquid obtained after the supercritical carbon dioxide reacts with the sample in the high-temperature high-pressure magnetic stirrer reactor 25, i.e., the reaction residual water source, can be used as a water source for a contact angle experiment, i.e., the contact angle test system 3, and the water source flows into the piston container 41, and further flows into the drip valve 36. The function of filling the tap water in the water tank 45 is to load a stream of water through the advection pump 44, which can provide a pressure to push a spring in the piston container 41 upward, and the upward movement of the spring can press the reaction residual water source in the piston container 41 into the drip valve 36.

The observation system 4 is connected with the contact angle test system 3 and is configured to acquire an included angle between the water source and the sample when contact reaction is carried out in the contact angle test system 3. The included angle is the contact angle which is configured to characterize a measure of a degree of wetting of an in-situ measurement in a supercritical carbon dioxide environment.

The observation system 4 includes a camera 46 and a processing module.

The camera 46 is connected with the contact angle test system 3 and is configured to acquire a sample surface image when the contact reaction is carried out in the contact angle test system.

The processing module is connected with the camera 46 and is configured to determine the included angle between the water source and sample according to the sample surface image.

In an embodiment, the observation system 4 further includes a light source 38. The light source 38 is arranged outside the contact angle test system 3 and is configured to provide light for the camera 46.

As shown in FIG. 2, a structure of the device provided by the present disclosure in practical application can be specifically as follows.

The device includes a carbon dioxide gas cylinder 5, a filter 6, a low-temperature constant-temperature water bath box 8, a carbon dioxide storage tank 9, a pressure gauge 10, a first emptying valve 11, a plunger pump 12, a second switch 13, a preheater 17, a high-temperature and high-pressure magnetic stirrer rector 25, a precooler 28, a backpressure system, a contact angle high-pressure chamber 37, a piston container 41, an advection pump 44 and a water tank 45. A left end of the carbon dioxide storage tank 9 is connected with the carbon dioxide gas cylinder 5 through an air inlet pipeline, and the carbon dioxide storage tank 9 is placed in the low-temperature constant-temperature water bath box 8. The air inlet pipeline is provided with the filter 6 and a first switch 7. An upper end of the carbon dioxide storage tank 9 is connected with the plunger pump 12 through a pipeline, and the pipeline is provided with the pressure gauge 10, the second switch 13 and the first emptying valve 11. A left end of the plunger pump 12 is connected with the preheater 17 through a pipeline, and the pipeline is provided with a second emptying valve 14, a check valve 15, an electric contact pressure gauge 16 and a third switch 18. A temperate control instrument 19 is arranged at the top of the preheater 17, and the preheater 17 is connected with the high-temperature high-pressure magnetic stirrer rector 25 through a pipeline, the preheater 17 is externally connected with a third emptying valve 20, and the pipeline is provided with a fourth switch 21, a safety valve 22, a first pressure sensor 23 and a resistor 24. The high-temperature high-pressure magnetic stirrer rector 25 is internally provided with a thermometer 26 and is externally provided with a temperature controller 27. A fourth emptying valve 31 is arranged at the bottom of the high-tempera-ture high-pressure magnetic stirrer rector 25, a right sidewall of the high-temperature high-pressure magnetic stirrer rector 25 is connected with a right sidewall of the contact angle high-pressure chamber 37 through a pipeline, and the pipeline is provided with two switches, i.e., a fifth switch 32 and a sixth switch 33, a pressure regulating valve 34 and a pressure sensor 35. The two switches, i.e., the fifth switch 32 and the sixth switch 33, are arranged at a left end of the pressure regulating valve 24 and a right end of the pressure sensor 35, respectively. A contact angle device is arranged in the contact angle high-pressure chamber 37, a customized drip valve 36 is arranged at the top of the contact angle high-pressure chamber 37, and the customized drip valve 36 is connected with a right end of the precooler 28 through a pipeline.

The backpressure system includes a backpressure valve 29 capable of controlling a pressure of the high-temperature high-pressure magnetic stirrer rector 25 in the heating process, and an outlet 30 for the reaction residual water source. A left end of the precooler 28 is connected with the backpressure valve 29, and the precooler 28 is connected with the low-temperature constant-temperature water bath box 8 through a circulating pipeline. The piston container 41 is arranged between the top of the contact angle high-pressure chamber 37 and the precooler 28 through a pipeline, and the pipeline is provided with an eighth switch 40. A fifth emptying valve 43 of the container is arranged at the piston container 41, and two pipelines are arranged at the bottom of the piston container 41. A left pipeline is connected with a right end of the advection pump 44 and is provided with a ninth switch 42. A right pipeline is provided with the fifth emptying valve 43 of the container, and a left end of the advection pump 44 is connected with the water tank 45.

The low-temperature constant-pressure water bath box 8, as a treatment component of the gaseous carbon dioxide, can liquefy the carbon dioxide gas from the carbon dioxide gas cylinder 5 and store the liquefied carbon dioxide in the carbon dioxide storage tank. The preheater 17 is configured to heat and vaporize liquid high-pressure carbon dioxide. The high-temperature high-pressure magnetic stirrer rector 25 is connected with the preheater 17 through a pipeline, and the preheater 17 is configured to provide gaseous carbon dioxide to the high-temperature high-pressure magnetic stirrer rector 25. The high-temperature high-pressure magnetic stirrer rector 25 is configured to provide an occasion for a reaction between the sample and the gaseous carbon dioxide. The precooler 28 is connected with the high-temperature high-pressure magnetic stirrer rector 25 through a pipeline and is configured to cool a hot fluid in the reactor and is enable the cooled hot fluid to flow into the backpressure valve, thus ensuring that a fluid temperature is within the working range of the backpressure valve. The high-temperature high-pressure magnetic stirrer rector 25 is connected with the fourth emptying valve 31 and the contact angle high-pressure chamber 37, and the residual carbon dioxide gas after the reaction between the carbon dioxide gas and the sample is finished can be directly discharged through the fourth emptying valve 31, or flow into the contact angle high-pressure chamber 37 through a pipeline to provide a carbon dioxide environment for a contact angle experiment.

The high-temperature high-pressure magnetic stirrer rector 25 is made of corrosion-resistant stainless steel, and the corrosiveness of the supercritical carbon dioxide has no influence on the high-temperature high-pressure magnetic stirrer rector 25.

The low-temperature constant-pressure water bath box 8 works at −20° C. to normal temperature and is configured to liquefy the carbon dioxide gas from a steel cylinder, so as to facilitate the transfer of the carbon dioxide.

The carbon dioxide storage tank 9 is made of stainless steel with high temperature resistance, high pressure resistance and corrosion resistance, which is convenient for storing liquid carbon dioxide.

The preheater 17 employs a Φ6 coil to raise the temperature, and a length of the coil is 5 meters, which is convenient for heating and vaporizing the liquid carbon dioxide.

The temperature control accuracy of a temperature control instrument 19 is ±0.5° C., so as to ensure the measurement accuracy and improve the accuracy in the experiment process.

A temperature sensor employs the thermometer 26, and the temperature sensor employs a K-type thermocouple with a measure of 0-1100° C.

The accuracy of the first pressure sensors 23 is ±0.1%, and the measure is 0-60 MPa, which can ensure the experimental high-pressure range, ensure the experimental accuracy, and improve the accuracy of the experimental process.

The backpressure system is made of stainless steel, and the outlet 30 for the reaction residual water source in the backpressure system has a pipe diameter of 4 mm, and the back pressure system can control a pressure of the reactor in the heating process.

A high-pressure window of the contact angle high-pressure chamber 37 is made of sapphire, and a sealing ring of the contact angle high-pressure chamber 37 is sealed with a spring seal made of a carbon dioxide-resistant material, so as to ensure the experiment safety.

A flexible heating jacket is sleeved outside the preheater 17 to ensure the accuracy in the experiment process. The temperature control accuracy of the flexible heating jacket is ±0.2° C., so as to ensure the measurement accuracy and improve the accuracy of the experiment process.

The temperature control accuracy of the temperature controller 27 is ±0.2° C., the temperature controller is provided with a PID (proportional-integral-derivative) auto-tuning function and over-temperature power-off protection to ensure the measurement accuracy and improve the accuracy of the experimental process.

The specific operation steps of the device are as follows.

In S1, pure carbon dioxide is introduced into the carbon dioxide storage tank through the filter, the low-temperature constant-temperature water bath box can liquefy the carbon dioxide into liquid carbon dioxide, and the liquid carbon dioxide can be pressurized by the plunger pump to flow into the preheater, the electric contact pressure gauge is configured to measure a pressure of the liquid carbon dioxide, the check valve is configured to control a flow direction of the liquid carbon dioxide, the preheater is configured to change the liquid carbon dioxide into gaseous carbon dioxide by increasing the temperature, and the switch is configured to control whether the carbon dioxide gas flows into the high-temperature high-pressure magnetic stirrer reactor or not.

In S2, the thermometer and the temperature controller are configured to control the temperature in the high-temperature high-pressure magnetic stirrer reactor, and the backpressure system is configured to control a pressure in the reactor in the heating process, the sample is placed in the high-temperature high-pressure magnetic stirrer reactor and reacts with the carbon dioxide gas, and the reaction residual water source after the reaction is drained through the emptying valve.

In S3, the switch on the pipeline on the right sidewall of the high-temperature high-pressure magnetic stirrer reactor is configured to control whether residual carbon dioxide after the reaction is introduced into the contact angle high-pressure chamber or not.

In S4, the switch at the pipeline on at the bottom wall of the high-temperature high-pressure magnetic stirrer reactor is configured to control whether the reaction residual water source after the reaction is introduced into the piston container.

In S5, the reaction residual water source obtained after the reaction in the high-temperature high-pressure magnetic stirrer reactor can be used as a solution for the contact angle experiment, and put into the piston container. Tap water is provided to the advection pump through the water tank, and the advection pump is loaded with a small flow rate of the tap water to drop the reaction residual water source in the piston container into the contact angle pressurized chamber.

In S6, an experimental sample is placed on contact angle device, and the carbon dioxide gas in the high-temperature high-pressure magnetic stirrer reactor is introduced into the contact angle high-pressure chamber. The contact angle experiment can be carried out when the contact angle high-pressure chamber is filled with the carbon dioxide gas.

In S7, an included angle θ between division lines of liquid and shale is captured by the high-speed camera, and a measure of the degree of wetting is designated as θ.

θ=0 means complete wetting; θ<90° means partial wetting or wetting, where the sample, i.e., the surface of the rock, is hydrophilic, the smaller the angle, the better the wettability; θ=90° is a division line of wetting or not; θ=90° means no wetting, where a surface of the rock is hydrophobic, the greater the angle, the poor the wettability; and θ=180° means no wetting at all.

In above measurement, by regulating the temperature and pressure of the measurement device, the state of the carbon dioxide gas is changed, when the carbon dioxide is above its critical temperature and critical pressure, the carbon dioxide is changed into supercritical. At the moment, the carbon dioxide is located at a state different from both gas and liquid, and the in-situ measurement of the absorption conditions of the liquid under the supercritical carbon dioxide environment can be achieved. By adopting the device shown in FIG. 2, a contact angle of the liquid on the surface of the sample, i.e., the rock, in the supercritical carbon dioxide environment at different temperatures and pressures can be obtained.

Specifically, taking deionized water and a shale sample as an example, the process of testing using the deionized water and the shale samples is as follows.

The preparation of the supercritical carbon dioxide and the reaction between the supercritical carbon dioxide and the rock are as follows.

All switches of the system are turned off, the first switch 7 is turned on to inject the carbon dioxide gas in the carbon dioxide gas cylinder 5 into the carbon dioxide storage tank 9, and the second switch 13, the third switch 18 and the fourth switch 21 are turned on to introduce the carbon dioxide into the high-temperature high-pressure magnetic stirrer reactor 25 for a reaction experiment between the supercritical carbon dioxide and the rock. The experimental temperature is changed through the temperature control instrument 19 and the temperature controller 27, and an experimental pressure is controlled through the first pressure sensor 23.

After the reaction between the supercritical carbon dioxide and the sample is finished, the fifth switch 32 is turned on to inject the supercritical carbon dioxide into the contact-angle high-pressure chamber 37. Meanwhile, the eighth switch 40 is turned on to inject the reaction residual water source into the piston container 41, e.g., deionized water. The ninth switch 42 is turned to convey the liquid in the piston container 41 into the customized drip valve 36. The temperature controller 27 is configured to regulate a temperature of a test device, i.e., the reaction system 2. The pressure regulating valve 34 is configured to regulate the pressure of the test device, i.e., the reaction system 2, thus making the carbon dioxide in the contact angle high-pressure chamber 37 reach a supercritical state. The liquid in the customized drip valve 36 is dripped on the surface of the shale sample placed in the contact angle high-pressure chamber 37. The camera 46 in the observation system 4 is configured to capture an image of the liquid on the shale surface, and the contact angle between the division lines of the liquid and shale is fit through a processing module, such as software.

Figure 3:
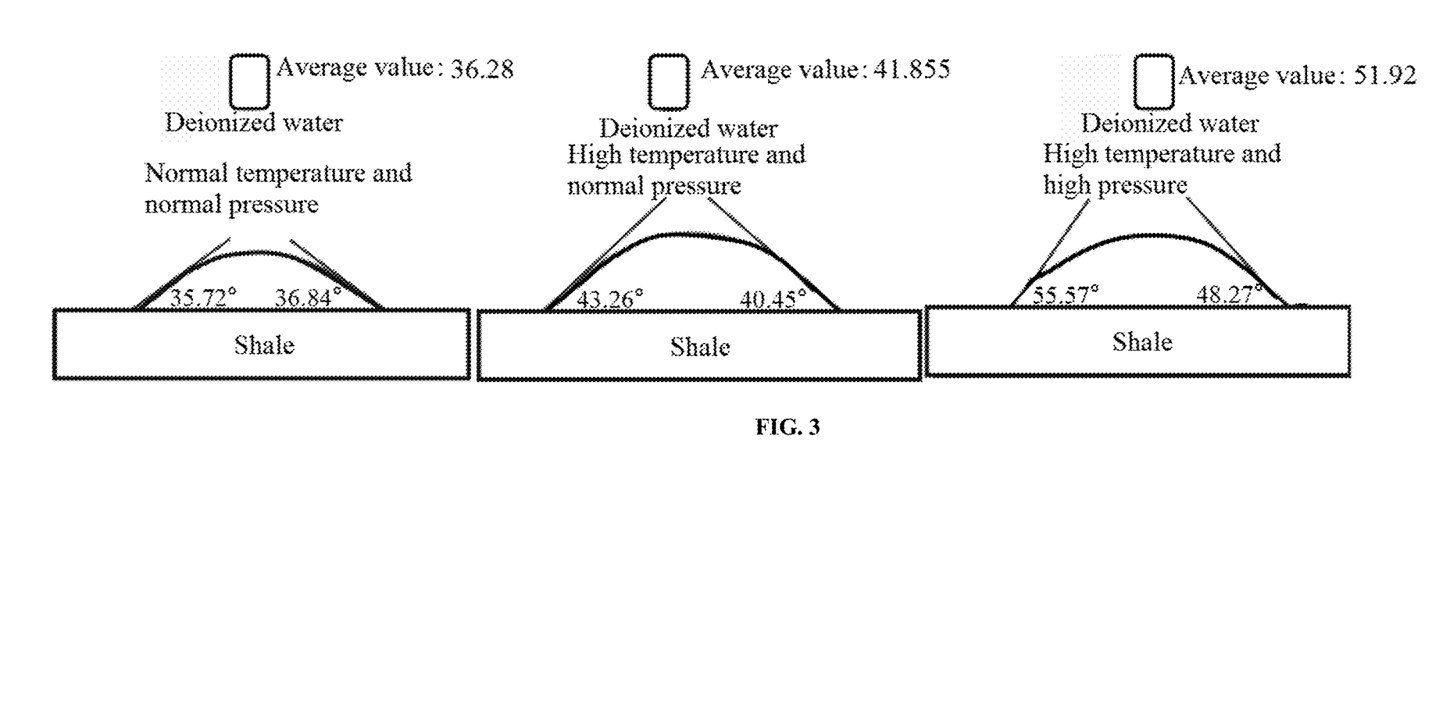
FIG. 3 is a schematic diagram of a contact angle experimental result according to the embodiment of the present disclosure.

As shown in FIG. 3, the deionized water and the shale are used as contact angle experimental materials, and the experimental conditions are controlled to be a normal temperature, a high temperature, and high temperature and high pressure, respectively. The contact angles of the deionized water on the shale surface are tested under the above three experimental conditions. The experimental results show that increasing temperature or pressure can reduce the wettability of the deionized water on the shale surface under the supercritical carbon dioxide environment.

The traditional experiment of measuring the contact angle of liquid on the rock surface under normal temperature and pressure conditions cannot provide an experimental environment full of the supercritical carbon dioxide for the experiment. In fact, the in-situ rocks are stored at a certain pressure and temperature, and there is a great error between the experiment and actual situations under the normal temperature and pressure. The embodiments have the advantages that test temperature and pressure can be directly controlled to simulate an in-situ environment for the reaction test between the supercritical carbon dioxide and the rock, which is helpful to study the storage, transportation and storage mechanism of the carbon dioxide in the shale or coal reservoirs. By controlling the temperature and pressure, the test is in an experimental environment of the supercritical carbon dioxide, which is helpful to study the wettability of the liquid-sample in a supercritical carbon dioxide atmosphere, characterizing the storage and transportation of the carbon dioxide in the shale and coal under a high-temperature high-pressure environment, and the influence of the supercritical carbon dioxide on a liquid contact angle under different temperature and pressure conditions.

The device provided by the embodiment of the present disclosure can achieve an in-situ reaction experiment of the sample and the supercritical carbon dioxide and a contact angle experiment under a supercritical carbon dioxide environment. The carbon dioxide storage tank is connected with the carbon dioxide gas cylinder through an air inlet pipeline and is placed in the low-temperature constant-temperature water bath box. The carbon dioxide storage tank is connected with the plunger pump through the pipeline, and the plunger pump is connected with the preheater through the pipeline. The temperature controller is arranged at the top of the preheater, and the preheater is connected with the high-temperature high-pressure magnetic stirrer reactor through the pipeline. The preheater is externally connected with the emptying valve, and the high-temperature high-pressure magnetic stirrer reactor is internally provided with the thermometer, and externally provided with the temperature controller. The bottom of the high-temperature high-pressure magnetic stirrer reactor is provided with the emptying valve, a right sidewall of the high-temperature high-pressure magnetic stirrer reactor is connected with a right sidewall of the contact angle high-pressure chamber through the pipeline, and two switches are placed at the left end of the pressure regulating valve and the right end of the pressure sensor, respectively. The contact angle device is arranged in the contact angle high-pressure chamber. The customized drip valve is arranged at the top of the contact angle high-pressure chamber and is connected with a right end of the precooler through a pipeline. The backpressure system includes the backpressure valve capable of controlling the pressure of the high-temperature high-pressure magnetic stirrer reactor in the heating process and the outlet for the reaction residual water source. The left end of the precooler is connected with the backpressure valve, the precooler is connected with the low-temperature constant-temperature water bath through a circulating pipeline, the piston container is arranged between the top of the contact angle high-pressure chamber and the precooler through a pipeline, the container emptying valve is arranged at the top of the piston container, and two pipelines are arranged at the bottom of the piston container. The left pipeline is connected with the right end of the advection pump, the container emptying valve is arranged on the right pipeline, and the left end of the advection pump is connected with the water tank. The device provided by the present disclosure can carry out reaction experiments of the supercritical carbon dioxide and the sample at different temperatures and pressures, and the contact angle experiment under the carbon dioxide environment can be carried out through the contact angle high-pressure chamber, so as to obtain the spreading condition of the liquid in the supercritical carbon dioxide atmosphere.

Various embodiments in this specification are described in a progressive way, and each embodiment focuses on the differences from other embodiments, so it is only necessary to refer to the same and similar parts between the embodiments.

Specific examples are used herein for illustration of the principles and embodiments of the present disclosure. The description of the embodiments is merely used to help illustrate the method and its core principles of the present disclosure. In addition, those of ordinary skill in the art can make changes in terms of specific embodiments and scope of application in accordance with the idea of the present disclosure. In conclusion, the content of this specification shall not be construed as a limitation to the present disclosure.

What is claimed is:

1. A device for testing a reaction between supercritical carbon dioxide and a rock, comprising:
   a carbon dioxide pressurization system configured to liquefy, heat and vaporize an initial carbon dioxide gas to obtain gaseous carbon dioxide;
   a reaction system connected with the carbon dioxide pressurization system and configured to regulate and control a temperature and a pressure to change a state of the gaseous carbon dioxide to obtain the supercritical carbon dioxide, and to enable the supercritical carbon dioxide to react with a sample, so as to obtain reaction products, wherein the reaction products comprise a reaction residual water source, a reaction sample and residual supercritical carbon dioxide;
   a contact angle test system connected with the reaction system and configured to convey the reaction residual water source, to receive the residual supercritical carbon dioxide, and to carry out a contact reaction of the residual supercritical carbon dioxide, the sample and the reaction residual water source; and an observation system connected with the contact angle test system and configured to acquire an included angle between the reaction residual water source and the sample when the contact reaction is carried out in the contact angle test system, wherein the included angle is configured to characterize a measure of a degree of wetting of an in-situ measurement in a supercritical carbon dioxide environment;

wherein the measure of the degree of wetting is designated as $\theta$; $\theta=0$ means complete wetting; $\theta<90°$ means partial wetting or wetting, where the sample is hydrophilic, and the smaller the included angle, the better the wettability; $\theta=90°$ is a division line of wetting or not; $\theta<90°$ means no wetting, where a surface of the rock is hydrophobic, the greater the included angle, the poor the wettability; and $\theta=180°$ means no wetting at all; and wherein the contact angle test system comprises:

a drip valve connected with the reaction system and configured to convey the reaction residual water source; and a contact-angle high-pressure chamber connected with the reaction system and the drip valve and configured to receive the residual supercritical carbon dioxide and the reaction residual water source, and to carry out the contact reaction of the residual supercritical carbon dioxide, the sample and the reaction residual water source.

2. The device for testing a reaction between supercritical carbon dioxide and a rock according to claim 1, wherein the carbon dioxide pressurization system comprises:

a low-temperature constant-temperature water bath box configured to liquefy the initial carbon dioxide gas to obtain liquefied carbon dioxide; and a preheater connected with the low-temperature constant-temperature water bath box and configured to heat and vaporize the liquefied carbon dioxide to obtain the gaseous carbon dioxide.

3. The device for testing a reaction between supercritical carbon dioxide and a rock according to claim 2, wherein the carbon dioxide pressurization system further comprises:

a carbon dioxide gas cylinder configured to provide the initial carbon dioxide gas; and a filter connected with the carbon dioxide gas cylinder, and configured to filter the initial carbon dioxide gas, and to convey the filtered carbon dioxide gas to the low-temperature constant-temperature water bath box.

4. The device for testing a reaction between supercritical carbon dioxide and a rock according to claim 1, wherein the reaction system further comprises a high-temperature high-pressure magnetic stirrer reactor, a thermometer, a temperature controller, a pressure regulating valve and a pressure sensor;

the high-temperature high-pressure magnetic stirrer reactor is connected with the carbon dioxide pressurization system, the thermometer is arranged inside the high-temperature high-pressure magnetic stirrer reactor, the temperature controller is arranged outside the high-temperature high-pressure magnetic stirrer reactor and is connected with the high-temperature high-pressure magnetic stirrer reactor; the pressure regulating valve is connected with the high-temperature high-pressure magnetic stirrer reactor, and the pressure sensor is connected with the pressure regulating valve;

the thermometer is configured to measure a temperature in the high-temperature high-pressure magnetic stirrer reactor;

the temperature controller is configured to regulate and control the temperature in the high-temperature high-pressure magnetic stirrer reactor;

the pressure regulating valve is configured to regulate and control a pressure in the high-temperature high-pressure magnetic stirrer reactor;

the pressure sensor is configured to measure the pressure in the high-temperature high-pressure magnetic stirrer reactor, and the high-temperature high-pressure magnetic stirrer reactor is configured to receive the gaseous carbon dioxide, and the sample is placed in the high-temperature high-pressure magnetic stirrer reactor; the state of the gaseous carbon dioxide in the high-temperature high-pressure magnetic stirrer reactor is changed to obtain the supercritical carbon dioxide; and in the high-temperature high-pressure magnetic stirrer reactor, the supercritical carbon dioxide reacts with the sample to obtain the reaction products.

5. The device for testing a reaction between supercritical carbon dioxide and a rock according to claim 4, wherein the contact angle test system further comprises:

a water tank configured to store tap water;

an advection pump connected with the water tank and configured to load the tap water according to a set flow rate; and a piston container connected with the advection pump, the drip valve and the high-temperature high-pressure magnetic stirrer reactor, and configured to receive the reaction residual water source and to convey the reaction residual water source to the drip valve by means of a pressure of loading the tap water by the advection pump.

6. The device for testing a reaction between supercritical carbon dioxide and a rock according to claim 1, wherein the observation system comprises:

a camera connected with the contact angle test system and configured to acquire a sample surface image when the contact reaction is carried out in the contact angle test system; and a processing module connected with the camera and configured to determine the included angle between a water source and the sample according to the sample surface image.

7. The device for testing a reaction between supercritical carbon dioxide and a rock according to claim 6, wherein the observation system further comprises a light source; and the light source is arranged outside the contact angle test system and is configured to provide light for the camera.

* * * * *